United States Patent [19]
Coggins et al.

[11] Patent Number: 5,217,494
[45] Date of Patent: Jun. 8, 1993

[54] TISSUE SUPPORTING PROSTHESIS

[76] Inventors: Peter R. Coggins, Suite B104-105, Greenville Center, Greenville, Del. 19807; Paul D. Brothers, 112 Mill Brook Dr., Chadds Ford, Pa. 19317

[21] Appl. No.: 681,430

[22] Filed: Apr. 5, 1991

Related U.S. Application Data

[63] Continuation-in-part of Ser. No. 296,250, Jan. 12, 1989, abandoned.

[51] Int. Cl.⁵ .............................................. A61F 2/02
[52] U.S. Cl. ........................................ 623/11; 623/66
[58] Field of Search ................. 623/11, 13, 14, 15, 623/16, 20, 1; 606/151, 153

[56] References Cited

U.S. PATENT DOCUMENTS

| | | | |
|---|---|---|---|
| 3,577,837 | 5/1971 | Bader, Jr. | 623/13 |
| 3,646,615 | 3/1972 | Ness | 623/14 |
| 3,688,317 | 9/1972 | Kurtz | 623/1 |
| 3,805,300 | 4/1974 | Tascon-Alonso et al. | 623/13 |
| 4,127,902 | 12/1978 | Homsy | 623/16 |
| 4,149,277 | 4/1979 | Bokros | 623/13 |
| 4,187,558 | 2/1980 | Dahlen et al. | 623/13 |
| 4,246,660 | 1/1981 | Wevers | 623/13 |
| 4,986,831 | 1/1991 | King et al. | 606/151 |

*Primary Examiner*—Randall L. Green
*Assistant Examiner*—Gina M. Gualtieri
*Attorney, Agent, or Firm*—Sixbey, Friedman, Leedom & Ferguson

[57] ABSTRACT

A prosthesis for supporting tissue and a method for implanting the prosthesis are disclosed wherein the prosthesis may be easily repositioned subsequent to implantation. The prosthesis is formed with a flexible core which is elastic in the longitudinal direction, and one end of the prosthesis is provided with a tissue ingrowth surface to receive tissue growth. The remainder of the prosthesis is covered with a biocompatible covering which tends to seal against sutures or other anchoring units which pierce the covering. The flexible cover is formed to accept such anchoring units without tearing.

15 Claims, 3 Drawing Sheets

TISSUE SUPPORTING PROSTHESIS

This application is a continuation-in-part application of U.S. patent application Ser. No. 07/296,250 filed Jan. 12, 1989, now abandoned.

FIELD OF THE INVENTION

A prosthesis for supporting tissue and the method for its implantation are disclosed herein. The prosthesis is used to tighten or lift loose or sagging tissue in cosmetic surgical procedures. One such procedure is commonly referred to as a "face lift". The prosthesis is not limited to use in that procedure, however.

BACKGROUND OF THE INVENTION

There is a rapidly increasing number of cosmetic surgeries conducted each year. Of these surgical procedures, one of the most frequent is the face lift or cervicoficial rhytidectomy. This procedure is time consuming, expensive and generally involves extensive tissue removal and typically requires 4 to 5 hours to complete. Examples of the conventional face lift procedure are discussed in: Sohn, S.A., Ed., *Fundamentals of Aesthetic Plastic Surgery*, Williams and Wilkins, Baltimore, MD (1987), pp. 127-157; Kay, B.L., *Facial Rejuvenation Surgery, A Color Photographic Atlas*. J.P. Lippincott, Philadelphia, PA (1987), pp. 22-63; and Georgiade, N.G., et al., Eds., *Essentials of Plastic. Maxillofacial. and Reconstructive Surgery*, Williams and Wilkins, Baltimore, MD (1987), pp. 533-557.

In a routine face lift, the tissues are stretched, and then anchored down to a semi-movable or stretchable focus to tighten or lift loose or sagging tissue. Over a period of time, however, the stretched tissue undergoes elastic degeneration and stretching whereby the tissue again becomes loose or sags. Thus, a conventional face lift may only last for a period of about three to six years. After this time, the entire face lift procedure must be repeated.

SUMMARY OF THE INVENTION

A tissue supporting prosthesis, which is implanted within a living being, comprises: means for adhering tissue to the prosthesis by tissue growth therein; means for anchoring the prosthesis to a solid structure; and means for interconnecting said adhering means and said anchoring means.

The purpose of the prosthesis is to overcome the inherent elasticity and memory loss of normal tissue by providing a device, which once implanted can be adjusted to tighten or lift loose or sagging tissue which has stretched after the implantation of the device, without re-performing the entire procedure.

The use of the prosthesis provides the following advantages over existing cosmetic surgical procedures:

1. It reduces the complexity of the procedure.
2. It allows minor adjustments to be made over the period of its implantation.
3. It is anchored at one end to the tissue which is to be supported by the growth of fibrous tissue into the prosthesis.
4. It is anchored at the other end to a solid or unmovable member of the body, such as fascia or bone.
5. It is somewhat elastic, in the longitudinal direction, to allow for movement of the body part to which the prosthesis is connected.

The prosthesis may be used in cosmetic surgical procedures other than face lifts. Those procedures include, but are not limited to: correction of breast ptosis (drooping); suspension of the buttock; suspension of the medial or the inner aspect of the leg; suspension of the area of the lip deformed secondarily to muscle paralysis; and suspension of the eyelid.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
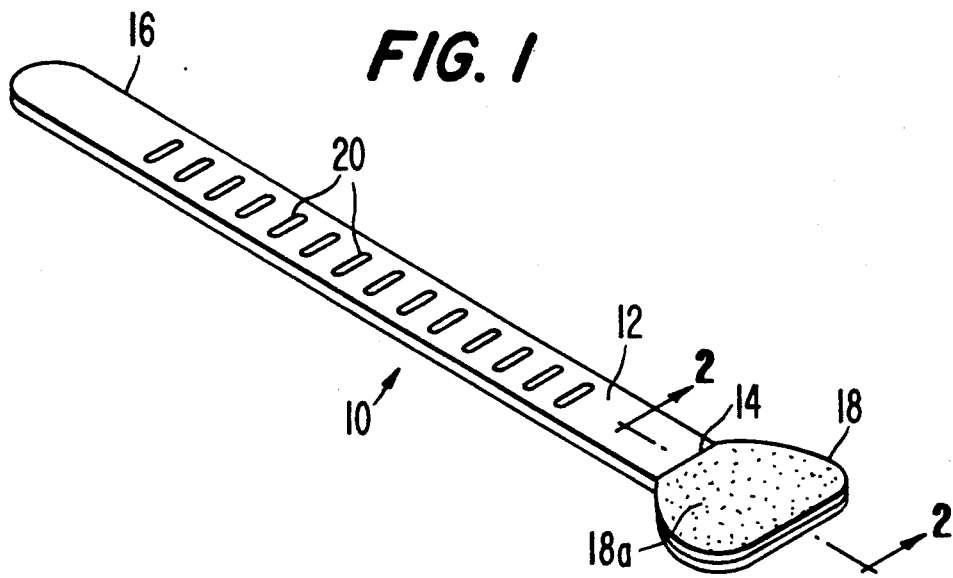
FIG. 1 is a perspective view of the tissue supporting prosthesis of the present invention.

Referring to the drawings wherein like numerals indicate like elements, there is shown in FIG. 1 a prosthesis 10. Prosthesis 10 preferably comprises an elongated flat band or body 12 which extends between a first end 14 and a second end 16. Band 12, alternatively, may be rod shaped or thread-like; its shape depends upon the area of the body into which the prosthesis is to be implanted as discussed below. A paddle 18 is integral with the first end 14 and is intended to be located within the human body adjacent the tissue which is to be supported so that the fibrous tissue will grow into and adhere to the paddle.

Figure 2:
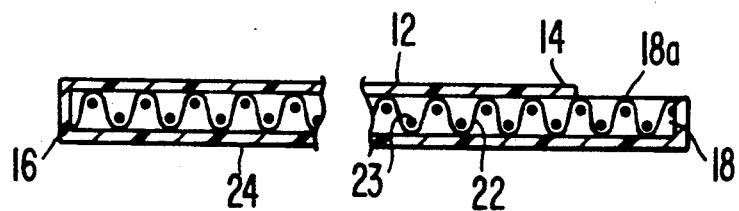
FIG. 2 is a sectional view of the prosthesis of FIG. 1.

Referring to FIG. 2, one embodiment of prosthesis 10 will be described. Band 12 interconnects paddle 18, that adheres to tissue, and second end 16, that is anchored to a solid structure. Band 12 is designed to have tensile strength along its longitudinal axis, but is flexible and slightly elastic so that it can stretch with body movement. Band 12 may also include surgical stainless steel wire or monofilament polyester fiber 20 secured thereto and laid perpendicular to the longitudinal axis of the band as reinforcing strips to minimize torsional bending while permitting the prosthesis to flex and stretch along the longitudinal axis thereof. The band is constructed with a core 22 and coating 24, and the reinforcing strips 20 may be secured to either. Core 22 may be made of a number of materials so long as it meets the criteria set forth above. Exemplary materials include: polyester (such as Hytrel®, Dacron®, Mylar®); polyimides (such as Kevlar®, Kapton®); and fluoropolymers (such as Teflon®), each of which is a trademarked product manufactured by the DuPont Company of Wilmington, Delaware. Although the materials forming the core 22 may be films, a woven fabric core is preferred, although the fabric can be felted, needle-punched, expanded or sintered. Coating 24 is preferably a silicone coating; silicone being chosen because tissue will not grow into it and therefore tissue will not adhere to it. Furthermore, silicone is self-healing in that its elastomeric memory will allow for closing of puncture openings made in the silicone coating layer.

Paddle 18, located at the first end 14 of band 12, must be so constructed that tissue will grow into a portion thereof. Referring to FIGS. 1 and 2, paddle 18 is shown as wider than band 12; but this is not always necessary, and the paddle may be the same width as band 12. At least one surface 18a of paddle 18 must be made of a material into which tissue may grow. These materials are typically porous and biocompatible so that tissue can grow therein.

In FIG. 2, core 22 is a woven fabric core and is shown extending into the paddle 18 to provide the surface 18a. In such a construction the core material is porous (to allow tissue growth therein) and biocompatible. If the core material does not meet these criteria or if a separate tissue ingrowth layer is desirable, then the core material must be covered with a biocompatible material and provided with a surface section which will allow tissue growth and which is also biocompatible. For example, a polyester coating layer may be adhered to the core material with an inert silicone adhesive. Also, the paddle 18 may be formed so that tissue can grow into both sides of the paddle.

As previously indicated, the core 22 may constitute a film of polyester or another of the previously identified plastic materials, but films have various deficiencies which are not experienced with a woven fabric core formed from threads or strands of the noted materials. Although pressed films may be oriented to possess tensile strength, they sacrifice tear resistance. If the end 16 of the prosthesis 10 is to be sutured in place, it is necessary to puncture this end with a suture. Sutures generally have a "saber tip" point which includes three edges extending angularly outward from the point. When a suture is pressed through a film, three cuts are made, each of which constitutes a potential point from which a tear can propagate. Films which are thick enough to resist tear propagation are often not sufficiently flexible. Since the tissue supporting prosthesis 10 is usually located near the skin surface, conformability is an important criteria if noticeable deformation due to the presence of the prosthesis is to be avoided. A thick, relatively rigid film prosthesis if used in the face area, for example, might cause noticeable deformation of the face when it is distorted during laughter, raising of an eyebrow, etc.

A core 22 formed from a precision woven fabric, such as the fabric 23 in FIG. 2, provides the balance of strength, flexibility and tear resistance not normally provided by a film core. By using a woven fabric for the core, severance of a few of the woven strands by a suture will not cause a tear, as the tear cannot propagate through adjacent undamaged threads. If a precision weave is used for the core fabric, a suture will often merely displace rather than cut the threads. If the threads of the fabric are oriented by stretching, they can exhibit both tensile strength and flexibility. By altering fabric orientation and/or the polyester, fluoropolymer, polyimide or other material forming the fabric threads, various degrees of constrained elasticity can be imparted to the tissue supporting prosthesis 10. This may be of great importance in applications such as an eyebrow lift where a minimal amount of force is to be placed on the prosthesis 10, but due to the large degree of eyebrow movement, the need for additional prosthesis conformity is required. Also, with a fabric core 22, a very thin prosthesis can be formed which is suitable for use in areas close to the surface of the skin such as in the forehead or eyebrow.

If the fabric core 22 is not biocompatible and/or doesn't possess enough structure to allow sufficient tissue ingrowth, it must be completely encapsulated in biocompatible material. Most of this encapsulating material will be the silicone layer 24, but at least at the end 14, this silicone layer will be replaced by an encapsulating biocompatible layer 26 of tissue ingrowth material which is secured to the fabric core 22 by a silicone adhesive. The tissue ingrowth material must be formed with voids or with some other construction which will receive tissue growth so that tissue will anchor the end 14 of the prosthesis 10. In many instances, tissue ingrowth material will be used with each woven fabric core 22, as the silicone adhesive will penetrate the fabric to securely anchor the tissue ingrowth layer.

Figure 3:
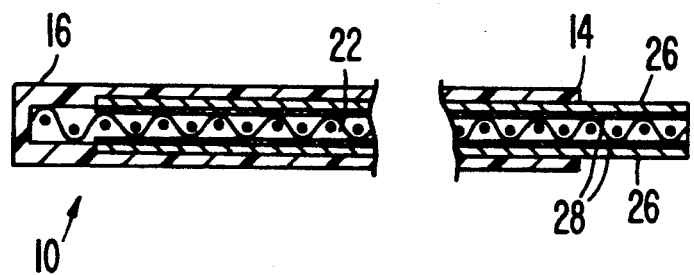
FIG. 3 is a sectional view of a second embodiment of the tissue supporting prosthesis of the present invention.

In FIG. 3, the prosthesis 10 is provided with separate tissue growth layers 26 secured by silicone adhesive 28 to the woven fabric core 22. It will be noted that the tissue ingrowth layers extend along a substantial length of the prosthesis 10, for example, for a distance at least one half the length, thus minimizing the thickness of silicone adhesive 28 required to secure the ingrowth material to the fabric core and thereby minimizing the thickness of the ingrowth material. Tissue will grow in through the exposed ends of the ingrowth material layer, but the silicone outer coating 24 will aid the silicone adhesive in preventing shear separation of the ingrowth material from the fabric core 22. If larger amounts of adhesive are used, the penetration of that adhesive into the ingrowth material results in less material available for tissue ingrowth. Since less (thinner) silicone adhesive is required in the paddle area, a thinner ingrowth material may be used. This minimization of the requirement for silicone adhesive facilitates the formation of a very thin prosthesis 10.

The dimensions and shape of the prosthesis may vary depending upon its use and placement within the body. For example, the prosthesis used in the face lift procedure may have an overall length of about 5 inches, a band width of about ⅛ inch and a band thickness of about 0.06 inches, and paddle dimensions of about ⅝ inch in length and about ¾ inch in width. Of course, if the prosthesis is to be used to lift or suspend the medial aspect of the leg, the paddle must be larger so that more tissue may grow therein and the band must be longer to extend between the area to be supported and the solid body to which it will be anchored. If the prosthesis is to be used to lift or suspend an eyelid or lip, the paddle must be smaller as less tissue weight needs to be supported and the band may be thinner and narrower, e.g., rod or thread like, so that it is not visible through the skin when implanted.

In general, the procedure for implanting the prosthesis is the same n matter where it is implanted within the body. The primary considerations are that the paddle 18 be implanted below the integument (skin) within tissue, e.g., the fascia, fascia and muscle, muscle, subcutaneous (superficial or deep) tissue, or SMAS (superficial musculoaponeurotic system), which can grow into and thereby adhere to the paddle, and that the second end be implanted next to a solid body, e.g., bone or fascia, so that the prosthesis may be anchored thereto. In the face lift procedure, the paddle 18 is implanted in the deep subcutaneous and SMAS tissues and the second end is attached to the cranium. In the breast lift procedure, the paddle is implanted deep into the breast tissue (so that the prosthesis mimics the Cooper's ligament) and the second end is attached to either the clavicle or the rib. In the lip suspension procedure, the paddle is implanted into muscle (orbicularis muscle) and the second end is attached to the temporal area of the skull. In the suspension of the medial aspect of the leg, the paddle is implanted into deep subcutaneous tissue and the second end is attached to the pelvic bone. In the suspension of the eyelid, the paddle is implanted in the tarsal plate and the second end is attached to the superior portion of the orbital rim. The above examples are not limiting as the paddle may be located into any tissue which will grow and adhere to the tissue receiving surface or surfaces of the paddle.

An incision is made through the integument intermediate the area into which the paddle 18 is to be located and the point at which the second end is to be anchored. Dissection from the incision to the area of tissue into which the paddle will be adhered is then carried out Dissection from the incision to the point at which the second end is to be anchored is then carried out. The paddle is then implanted into the first dissected area and sutured into place to prevent movement during tissue growth into the paddle. The second end 16 is then implanted into the second dissected area and sutured into place to prevent movement until anchoring to the solid body. The incision is then closed, in layer as is known, and any excess tissue is excised. A period of time, e.g., about one and one half months, is allowed to lapse so that tissue may grow into the paddle. Thereafter, an incision is made over the second end 16 so as to expose that end and the solid body to which it is to be attached. The prosthesis is then retracted, so as to lift or tighten the tissue to be supported and the second end is anchored to the solid body by sutures or other attaching means. The second incision is then closed in a conventional manner. Subsequently, if the area supported begins to sag or loosen, the prosthesis may be retracted again by reopening the second incision and re-anchoring the second end 16 of the prosthesis.

Figure 4:
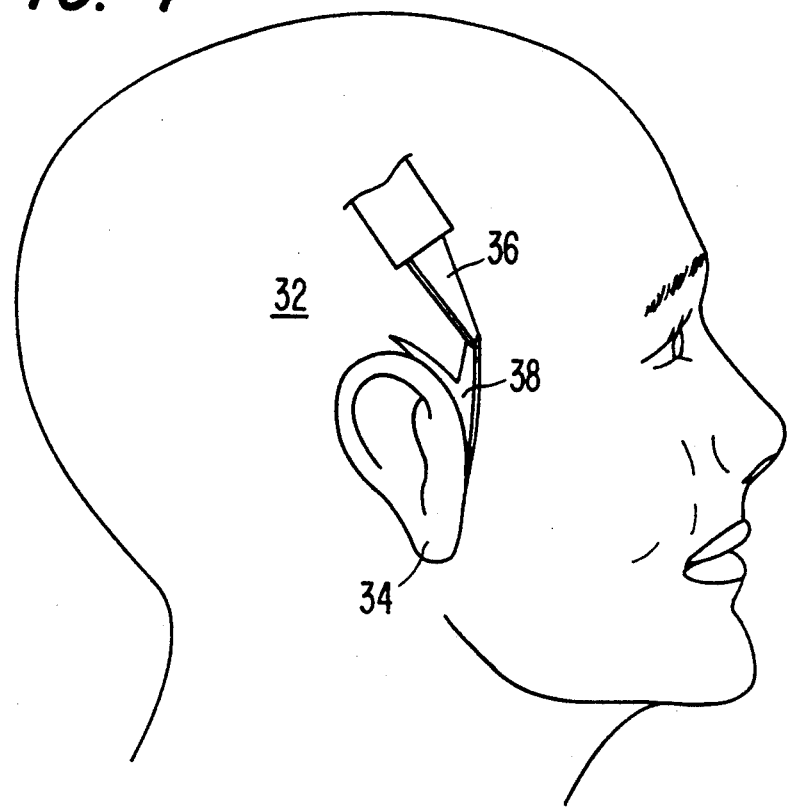
FIGS. 4-7 illustrate the face lift procedure in which the tissue supporting prosthesis is implanted.
Figure 5:
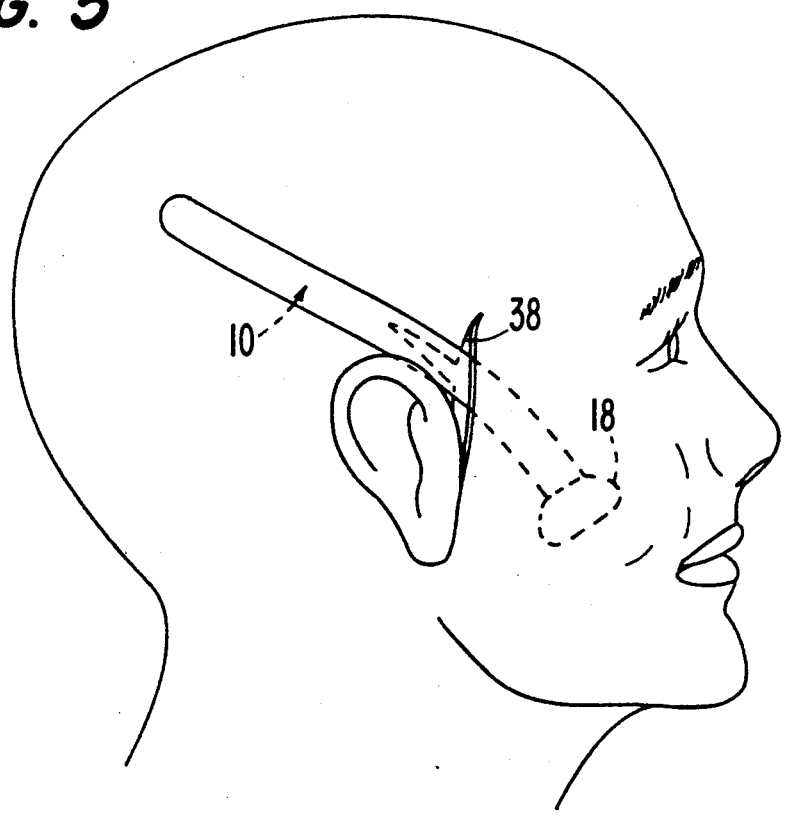
Figure 6:
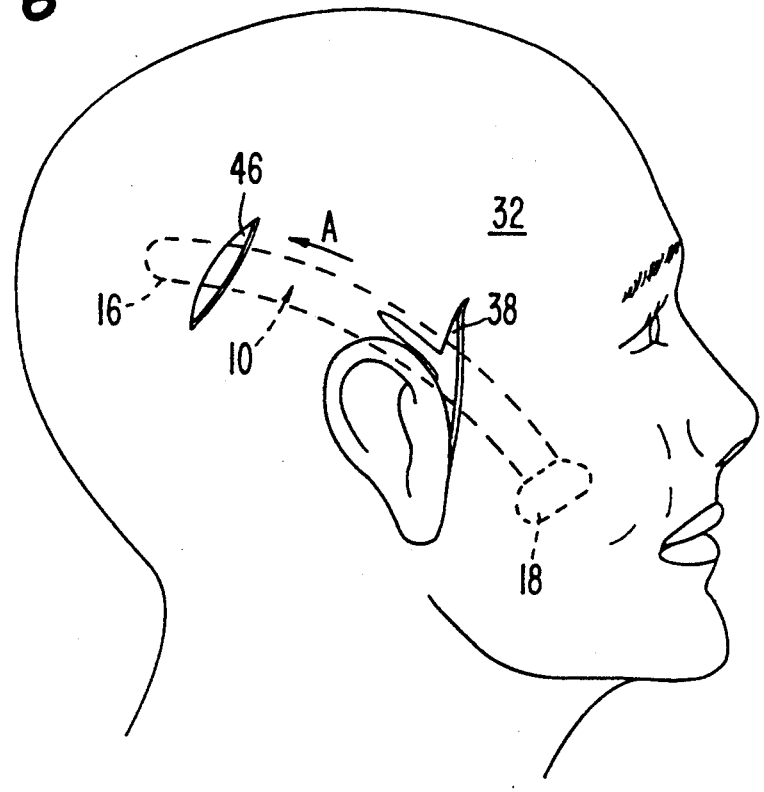
Figure 7:
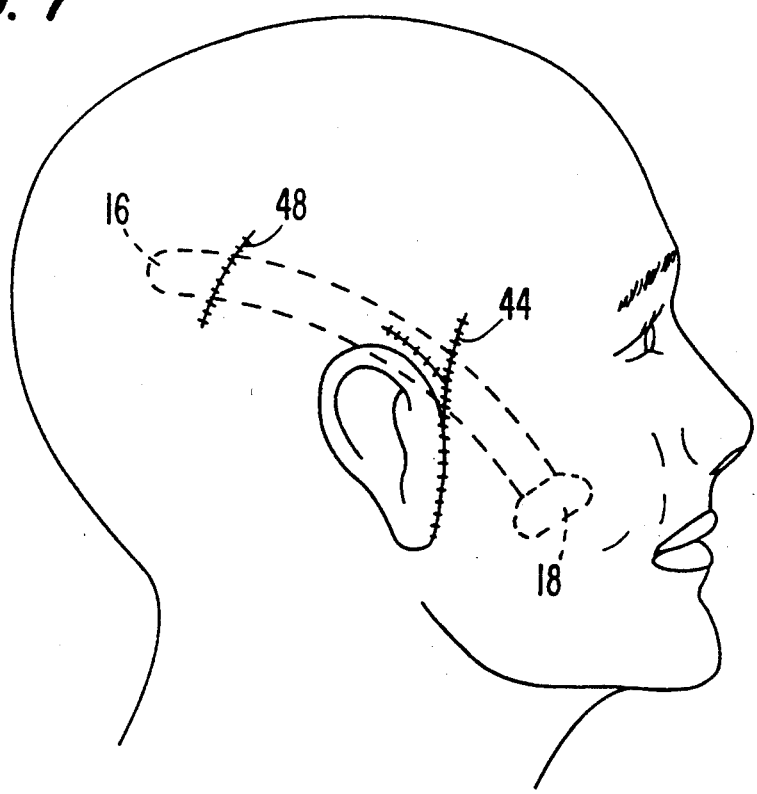

Referring to FIGS. 4-9, the procedure for implanting the prosthesis 10, specifically a face lift, is illustrated. In FIG. 4, an incision 38 is made, with a scalpel 36, through the integument along ear 34 of head 32. Dissection below the integument and into the subcutaneous tissue into the loose or sagging area of tissue is performed. Then, dissection into the area in which the prosthesis is to be anchored to a solid body is performed. In FIG. 5, the paddle 18 of the prosthesis 10 is then inserted through incision 38 into the fascia adjacent the sagging tissue and sutured thereto. In FIG. 6, the second end 16 of the prosthesis 10 is then inserted through incision 38 into the dissected area adjacent the solid body. In FIG. 7, incision 38 is closed with sutures 44. After a period of approximately one and one-half months, during which tissue grows into either the exposed core of the paddle 18, or the tissue growth layer 26, an incision 46 is made over the second end 16 of the prosthesis 10 (see FIG. 6). Prosthesis 10 is retracted (in the general direction of arrow A). A suture is used to anchor the second end 16 of the prosthesis 10 to the solid body after the sagging tissue has been pulled into shape. Thereafter, incision 46 is closed with sutures 48 (see FIG. 7).

As will be noted from FIGS. 1-3, the end 16 of the prosthesis 10 is completely enclosed by the silicone coating 24, and no openings are provided to receive tissue growth which would permit the end 16 to be anchored by tissue. Instead, the silicone coating rejects and prohibits tissue growth and further prevents tissue from growing into any suture openings in the end 16. In the past, when a prosthesis not constructed with a woven core was sutured in place, tissue would often grow into the small openings caused by the suture. However, in the prosthesis 10 of the present invention, the coating 24 is a soft, elastomeric silicone coating of known type which, when pierced, tends to rebound into the resultant opening and, because the woven core construction resists tear, the resultant opening is minimal. Thus, the elastomeric coating closes and seals the opening around the suture or fastener used, thereby preventing tissue ingrowth at the end 16 of the prosthesis 10. Consequently, the suture or fastener at the end 16 can be easily removed and the prosthesis adjusted if it is necessary to subsequently retract and re-anchor the end 16.

EXAMPLE

The patient is prepped and draped in a supine position under local anesthetic, such as 1% zylocaine anesthetic. An incision is made in the temporal scalp near and above the ear, continuing down the superior pole of the ear into the targus, proceeding around the edge of the targus to the inferior pole of the ear. Dissection is then carried out in the superficial subcutaneous tissues over the molar eminence and immediately beneath it. Dissection is then carried out, lateral to the orbit into the deeper scalp layer immediately above the temporal fascia. The paddle end of the prosthesis is then taken and fixed with 4 and 5.0 vicryl sutures to the superficial fascia immediately overlying the parotid gland. Secondary attachment on a more superficial plane can be obtained with a paddle in which either the core is exposed on both sides or both sides are provided with an ingrowth layer 26 as shown in FIG. 3. The second end of the prosthesis is then taken and placed at a point above the superior pole of the ear in the posterior portion of the scalp incision where a pocket is developed beneath the scalp directly over the temporal muscle on the skull. The second end of the prosthesis is tailored to an appropriate length and sutured into place either with 3.0 nylon, 3.0 wire or an inset with superficial screws into the cranium. The wound is then closed in layers as per a normal face lift procedure with the excision of excess scalp and preauricular tissue.

About one and one-half months later, adjustment is made with an opening up of the wound in the temporal scalp. The prosthesis is then retracted superiorly and posteriorly thereby tightening up the soft tissue of the face. Fibrous tissue has now grown into the paddle on one or both sides and a firm adherence is obtained. Once it has been moved back, the nylon or wires are reset and the wound is closed with 3.0 nylon. Adjustment can be made at any time through a simple incision in the scalp directly over the second end of the prosthesis.

The present invention may be embodied in other specific forms without departing from the spirit or essential attributes thereof and, accordingly, reference should be made to the appended claims, rather than to the foregoing specifications, as indicating the scope of the invention.

We claim:

1. A tissue supporting prosthesis which is adapted for implantation within a living being and is intended to be secured in part by tissue from said living being comprising:
   a core of flexible woven fabric material having a first end section and a second end section spaced from said first end section, an additional layer formed of biologically acceptable tissue ingrowth material into which tissue from said living being will grow attached to said core and extending to the first end section thereof to provide at said first end section surface means into which tissue will grow, and an outer cover layer of material which resists tissue ingrowth formed on said core and encapsulating said core and additional layer completely except in the area of said surface means of the layer of biologically acceptable tissue ingrowth material to provide an outer layer with no openings therein for the ingrowth of tissue, said cover layer including an opening to expose said surface means at said first end section to permit tissue to grow into said layer of tissue ingrowth material at said first end section only, said layer of tissue ingrowth material being secured to said core and extending from said first end section of said core beneath said outer cover layer toward said second end section for a predetermined distance.

2. The tissue supporting prosthesis of claim 1, wherein said outer cover layer is formed of material which, when pierced by an object, sealingly engages the object piercing said outer cover layer.

3. The tissue supporting prosthesis of claim 2, wherein said outer cover layer is formed of silicone.

4. The tissue supporting prosthesis of claim 1, wherein said woven fabric is formed from threads of a polyester, polyimide or fluoropolymer.

5. The tissue supporting prosthesis of claim 1, wherein said core is an elongate core having a longitudinal axis extending between said first and second end sections, said core having elasticity in the direction of said longitudinal axis.

6. The tissue supporting prosthesis of claim 5, which includes spaced reinforcing means extending substantially perpendicular to the longitudinal axis of said core to minimize torsional bending of said prosthesis.

7. The tissue supporting prosthesis of claim 1, wherein said tissue ingrowth material is provided on opposite sides of said core at said first end section.

8. The tissue supporting prosthesis of claim 1, wherein said tissue ingrowth material is secured to said core by a silicone adhesive.

9. The tissue supporting prosthesis of claim 1, wherein said core ,is a, flat, elongated fabric strip having a length, said length extending between said first and second end sections along a longitudinal axis, said fabric being formed to have elasticity in the direction of said longitudinal axis, and spaced reinforcing means extending substantially perpendicular to the longitudinal axis of said core along the length of said core between said first and second end sections to minimize torsional bending of said prosthesis.

10. A tissue supporting prosthesis which is adapted for implantation within a living being and is intended to be secured after implantation at one end by tissue ingrowth from said living being comprising:

an elongated core of flexible material having a first end, a second end, and a longitudinal axis extending between said first and second ends, said core being formed to have elasticity in the direction of said longitudinal axis, at least one additional elongated layer of tissue ingrowth material on said core, said elongated layer having a length and providing surface means at the first end of said core formed of biologically acceptable tissue ingrowth material into which tissue from said living being will grow, said layer of tissue ingrowth material being secured to said core along the extend of the length of said layer, and an outer cover layer of material which resists tissue ingrowth formed on said core encapsulates said core completely except in the area of said surface means of biologically acceptable tissue ingrowth material at said first end of said core to provide an outer layer with no openings therein for the ingrowth of tissue, the outer cover layer including an opening to expose said surface means to permit tissue ingrowth, said layer of tissue ingrowth material extending from said first end of said core beneath said outer cover layer toward said second end for a substantial distance.

11. The tissue supporting prosthesis of claim 10, which includes spaced reinforcing means extending substantially perpendicular to the longitudinal axis of said core to minimize torsional bending of said prosthesis.

12. A tissue supporting prosthesis which is adapted for implantation within a living being and is intended to be in part by tissue from said living being comprising:

a core of flexible woven fabric material formed of biologically acceptable tissue ingrowth material having a first end section and a second end section spaced from said first end section, said core being a flat, elongated fabric strip having a length, said length extending between said first and second end sections along a longitudinal axis, said fabric strip being formed to have elasticity in the direction of said longitudinal axis, spaced reinforcing means extending substantially perpendicular to the longitudinal axis of said core along the length of said core between said first and second end sections to minimize torsional bending of said prosthesis, and an outer cover layer of material which resists tissue ingrowth formed on said core and completely encapsulating said core except in an area of said first end section to provide an outer layer with no openings therein for the ingrowth of tissue, said outer cover layer being constructed to expose said core only at said first end section and being formed of a material which, when pierced by an object, sealingly engages the object piercing said outer cover layer.

13. A tissue supporting prosthesis which is adapted for implantation within a living being and is intended to be secured in part by tissue from said living being and in part solely by sutures or similar attachment units which pierce and extend through said prosthesis comprising:

a core of porous, biocompatible, tissue ingrowth material into which tissue from said living being will grow which includes, a first end section and a second end section spaced from said first end section, said core being a flat, elongated strip having a longitudinal axis extending between said first and second end sections and having elasticity in the direction of said longitudinal axis, and an outer cover layer of material which resists tissue ingrowth completely encapsulating said core except at said first end section thereof, at least one opening formed in said outer cover layer at said first end section to expose said core at only said first end section, said outer cover layer being formed of a material having an elastic memory which causes such material to engage and seal around an attachment unit which pierces said prosthesis and extends through said outer cover layer to close any opening in said outer cover layer resulting from said piercing so as to prevent tissue ingrowth about said attachment unit.

14. The tissue supporting prosthesis of claim 13 wherein said core is a woven fabric.

15. The tissue supporting prosthesis of claim 14 wherein said outer cover layer is a silicone layer.

* * * * *